United States Patent [19]
Phillips

[11] Patent Number: 5,290,297
[45] Date of Patent: Mar. 1, 1994

[54] SURGICAL FASTENER SYSTEM

[76] Inventor: Edward H. Phillips, 712 N. Roxbury Dr., Beverly Hills, Calif. 90210

[21] Appl. No.: 41,552

[22] Filed: Apr. 2, 1993

Related U.S. Application Data

[62] Division of Ser. No. 681,685, Apr. 5, 1991, Pat. No. 5,203,864.

[51] Int. Cl.⁵ .............................................. A61B 17/00
[52] U.S. Cl. ................................... 606/144; 606/151; 606/1; 24/711.1
[58] Field of Search .............. 606/144, 145, 151, 219, 606/220, 232, 1; 24/711.1

[56] References Cited

U.S. PATENT DOCUMENTS

| | | | |
|---|---|---|---|
| 312,199 | 2/1889 | Ginter | 227/137 |
| 2,222,125 | 11/1940 | Stehlik | 227/137 |
| 3,875,648 | 4/1975 | Bone | 606/221 |
| 4,121,487 | 10/1978 | Bone | 606/232 |
| 4,235,238 | 11/1980 | Ogiu et al. | 606/145 |
| 4,471,781 | 9/1984 | DiGiovanni et al. | 606/145 |
| 4,669,473 | 6/1987 | Richards et al. | 606/232 |
| 4,721,103 | 1/1988 | Freedland | 606/86 |
| 4,741,330 | 5/1988 | Hayhurst | 606/144 |
| 5,059,206 | 10/1991 | Winters | 606/220 |

*Primary Examiner*—Stephen C. Pellegrino
*Assistant Examiner*—Gary Jackson
*Attorney, Agent, or Firm*—Frederick Gotha

[57] ABSTRACT

A fastener system utilizes an H-shaped fastener which is composed of a pair of shaft members having a diameter of approximately 1 mm that are interconnected by a bridge shaft resiliently joined to the shaft members to form the H-shape. The shaft members have sufficient columnar resistence to bending to permit a shaft member to be compressively inserted into body tissue. A fixation tool carries the fastener for injection into body tissue and has a housing with a needle tip of approximately 5 mm in length. The needle tip has a longitudinally extending slot into which the bridge shaft of the H-shaped fastener member is captively held by interference fit. A setting rod is extendible through the needle tip and bears against a shaft of the H-shaped fastener such that an external force applied to the setting rod will be transmitted to the fastener to drive it into the body tissue.

4 Claims, 9 Drawing Sheets

SURGICAL FASTENER SYSTEM

This application is a divisional application of application Ser. No. 07/681,685 filed Apr. 5, 1991, now U.S. Pat. No. 5,203,864.

FIELD OF THE INVENTION

This invention relates primarily to a fastener system and method for use in laparoscopic surgical repair of inguinal herniation and for use in suturing body tissue to body tissue.

BACKGROUND OF THE INVENTION

Surgical treatment of inguinal herniae traditionally involved the removal or excision of the peritoneal sac and the strengthening of the weakened inguinal canal by performing a herniotoy, hernioplasty, or herniorrhaphy; in the case of inguinal herniae, the surgical technique entailed the excision of the femoral sac and either closing the margins of the internal ring or excluding it from continuity with the abdominal cavity. In some of these cases simple suture could not successfully close the hernia defect and a relaxing incision was required in the rectus sheath to bring the tissues together and allow the defect to be closed without tension. Where however, the patient's groin had been destroyed by repeated herniation and surgery, a mesh prosthesis made of polypropylene was used as a substitute for the relaxing incision.

Insertion of a polypropylene mesh prosthesis for the repair of inquinal herniae required a transverse incision through the abdominal wall in order to introduce the mesh into the preperitoneal space and subsequently to suture the anterior femoral sheath, and the iliac fascia and encompassed the floor of the inguinal canal extending from the pubic tubercle laterally to the femoral vein along the superior pubic ramus, superiorly to the transversus arch, and laterally to beyond the internal inguinal ring. The sutures to Cooper's ligament, the anterior femoral sheath and the iliac fascia required the knots to be tied posterially of the abdominal wall. Sutures were also required to be passed through the rectus muscle and the rectus sheath and tied anteriorly. Cephaled sutures were also necessary which incorporated a folded edge of the polyprophylene mesh and also closed the transverse incision which was used for access to the preperitoneal space.

SUMMARY OF THE INVENTION

There is, therefore, provided according to the present invention, a surgical fastener system for laparoscopically fixing a mesh prosthesis to body tissue for the laparoscopic repair of inguinal herniation or for other types of repair requiring the fixing of body tissue to body tissue non-laparoscopically. The present invention is directed to a uni-directional dart-type fastener in one embodiment where the dart fastener is composed of a shaft member having a diameter of approximately 1 mm and having a radially extending head or disk at one end and an anchor member angularly inclined to the shaft at its other end. The anchor member is resiliently collapsible radially to the shaft and biased in an open position which permits the anchor member to collapse radially during the dart's penetration of body tissue and permits it to be captively held uni-directionally within the body fascia. The dart fastener may be made of materials such as of polypropylene, stainless steel, or polydioxanone suture (PDS®) which is a trademark of Johnson and Johnson. In order to set the dart fastener laparoscopically, a dart fixation tool is provided which may be introduced into the space between the peritoneum and posterior abdominal wall through a trocar having an internal diameter of approximately 5 mm.

The dart fixation tool is composed of a cylindrical housing which has a cartridge rotationally carried at its distal end. The cartridge has a series of cylindrical chambers for carrying an individual dart fastener and are equally spaced radially and located adjacent to the periphery of the cartridge in a manner similar to the cartridge chambers of a revolver. A drive shaft extends longitudinally through the housing to rotate the cartridge and index each chamber into alignment with a setting rod which also extends longitudinally through the housing. The setting rod is slideably mounted in the housing and capable of extending through the aligned chamber of the cartridge by a thrust or external force applied to the setting rod by the surgeon. Each chamber is loadable with a single dart fastener which is captively held in the chamber by a leaf spring; by pushing on the setting rod the surgeon forces the rod to extend through the chamber thereby overcoming the resistance of the leaf spring and ejecting the dart fastener from the chamber. The setting rod is thereafter retracted from the chamber and the cartridge is rotated by the surgeon to bring the adjacent succeeding chamber into alignment with the longitudinal bore containing the setting rod.

Another embodiment of the dart fixation tool provides a tool which captively carries a single dart fastener by interference fit or by leaf spring retention located adjacent the distal end of the tool housing. A cavity or passage extends axially through the housing and a plunger which extends through the cavity transmits the external thrust force applied by the surgeon at the proximate end of the tool to the fastener to eject the fastener from the tool.

In another embodiment of the invention, an H-shaped fixation surgical fastener is provided for attaching polypropylene mesh to body tissue. The fastener is composed of a pair of shaft members having a diameter of approximately 1 mm which are interconnected by a bridge shaft which is resiliently joined to the shaft members to form an H-shaped member which is internally biased to retain the H configuration. To accommodate driving the fastener into the resistance of body tissue, the shaft members have sufficient columnar resistance to bending to permit a shaft member to be compressively inserted into body tissue. The H-shaped fastener may be made of materials such as polypropylene, stainless steel, or polydioxanone suture (PDS®) which is a trademark of Johnson and Johnson.

The H-shaped fastener is introduced into the preperitoneal operative space by a fixation tool composed of a housing which has a longitudinal axis, a proximate and distal end, and an axially extending cavity or passage through the housing. At its distal end, the housing contains a needle member which has an axial length of approximately 5 mm. An axially extending conduit extends through the needle member and communicates with the housing cavity. The needle member has a longitudinally extending slot which communicates with the conduit. At the distal end of the needle tip the slot is open which allows the bridge shaft of the H-shaped fastener member to extend through the slot when either shaft member of the H-shaped fastener is inserted into the needle tip of the housing. To set the fastener, a setting rod extends through the cavity of the housing and is slideably mounted to the housing so that the distal end of the setting rod may be selectively extended through the needle member conduit. The H-shaped fastener is captively held in the needle tip by interference fit and introduced into the preperitoneal operative region by inserting the fixation tool through a trocar.

To insert the H-shaped fastener into body tissue, the needle tip of the tool is manipulated to pass through an interstice of the mesh prosthesis and the surgeon then applies an external force to the setting rod to thrust the rod which in turn applies a compressive force against the driven shaft of the captively held H-type fastener thereby ejecting the fastener from the needle tip while pressing the driven shaft into the body tissue. The material of the H-shaped fastener has the property of a sufficient modulus of resilience to restore the H-shape such that the undriven shaft of the H-shaped fastener will bear against the mesh while the driven shaft will be biased toward a position within the fascia essentially parallel to the undriven shaft with the bridge member extending through an interstice of the mesh.

A method for laparoscopically attaching a mesh prosthesis to body tissue to repair inguinal herniation utilizing the fastener system of this invention provides for forming a retroperitoneal space by the injection of carbon dioxide gas through a Verress needle positioned in the suprapubic region, separating the peritoneum from the posterior abdominal wall, inserting a laparoscope into the retroperitoneal space, inserting a mesh prosthesis into the space and positioning the mesh to overlay the pelvis, and fixing the mesh to the posterior abdominal wall by sufficiently inserting a fastener through a mesh interstice so as to bear against the mesh and penetrate into the body tissue.

Thus, a fastener system is provided to repair inquinal herniae laparoscopically without the necessity of suturing the mesh by tying knots anteriorly or posterially of the abdominal wall. The mesh is introduced laparoscopically into the preperitoneal space and simply fastened to Cooper's ligament, the iliac fascia, and the abdominal wall to repair the inquinal or femoral hernia. Although the fastener system of this invention has a particular use to repair inguinal herniae, it may also be utilized for non-laparoscopic repairs to body tissue.

BRIEF DESCRIPTION OF THE DRAWINGS

These and other features and advantages will become appreciated as the same become better understood with reference to the following specification, claims and drawings wherein:

DETAILED DESCRIPTION

Laparoscopically guided preperitoneal hernia repair as performed in the present invention requires that the surgeon insufflate the intraperitoneal cavity with carbon dioxide gas until 15–18 mm Hg pressure. When the pressure is achieved, a 10 mm trocar is inserted into the peritoneal cavity through which a 10 mm 30-degree angle laparoscope is inserted and a TV camera attached. After a general abdominal exploration, the camera is pointed toward the pelvis. In the suprapubic location, a Verress needle (not shown) for gas injection is then inserted beneath the posterior abdominal wall but not through the peritoneum and carbon dixoide gas is thereafter injected through the needle into the space between the peritoneum and posterior abdominal wall until a small cavity i created. The needle is then removed and a 10 mm trocar is inserted into the cavity or retroperitoneal space between the peritoneum and posterial abdominal wall to accommodate the insertion of a reducer having a blunt probe (not shown) which is used to sweep the peritoneum from the underside of the abdominal wall.

The sweeping of the peritoneum from the abdominal wall is done bilaterally. If the right inguinal region is approached first for sweeping, the peritoneum is swept from the underside of the aponeurotic sling, more inferiorily the underside of the direct floor transversalis fascia and then the inguinal ligament, and then the femoral canal and the iliopubic tract which is the superior pubic ramus fascia. Using blunt dissection, the peritoneum is taken off the inguinal cord as it enters the peritoneal cavity. The same procedure is then followed on the left side of the pelvis. To 5 mm trocars (not shown) are then placed between the lower abdominal wall and the peritoneum in the left and right midclavicular lines respectively in the pelvis and into the cavity. A 5 mm laparoscope is then inserted through either of the 5 mm trocars, depending upon the location of the inguinal hernia to provide for observation of the region. A sheet of plastic mesh preferably polypropylene is now introduced into the cavity between the peritoneum and posterior abdominal wall through the 10 mm trocar which had been originally placed in the midline in the suprapubic position. After the mesh is introduced into the cavity, a 10 mm laparoscope with 30-degree angle lens is then inserted into the 10 mm site, and two graspers are inserted, one through each of the 5 mm trocars to manipulate the polypropylene mesh sheet within the cavity such that the mesh overlays the pelvis.

Figure 12:
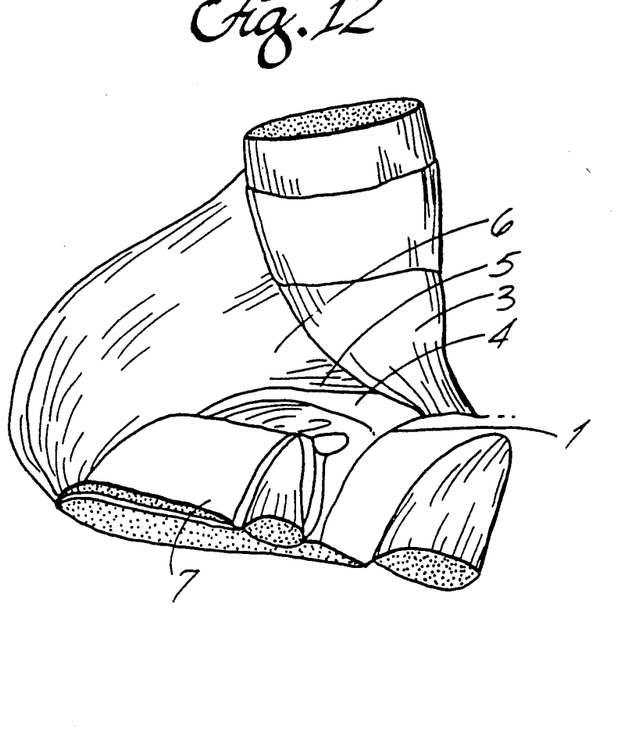
FIG. 12 is a posterior view of the left inguinal region of the human body.

FIG. 12 is an illustration of a posterior view of the left inguinal region showing Cooper's ligament 1, femoral ring 2, transversus abdominis muscle 3, posterior inguinal wall 4, conjoint tendon 5, the posterior abdominal wall 6, and the iliac fascia 7 before attachment of the mesh prosthesis. The right inguinal region is a mirror image of the left.

Figure 13:
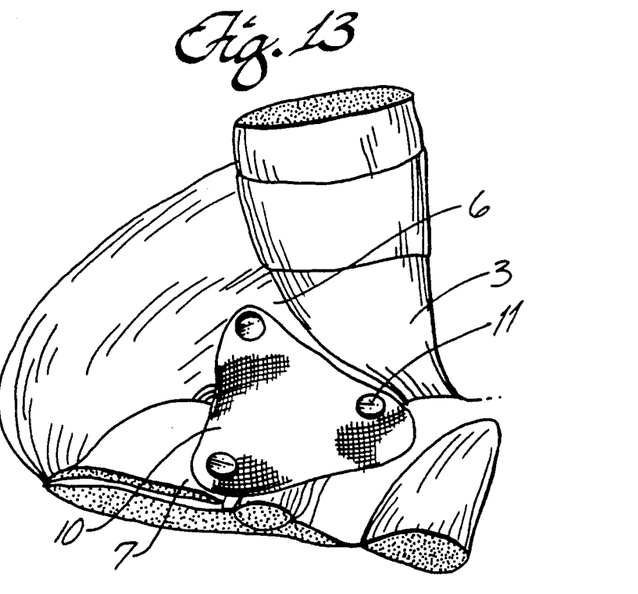
FIG. 13 illustrates a preperitoneal placement and fixation of a mesh prosthesis in the region depicted in FIG. 12.

FIG. 13 illustrates the laparoscopic placement of a mesh prostheses 10 which is fastened to Cooper's ligament 1 by a dart fastener 11 of this invention. Similarly, other portions of the mesh prosthesis 10 are fastened to the posterior abdominal wall 6 and the iliac fascia 7. Although FIG. 13 illustrates the mesh fastened to the left, the mesh may extend across to the right region thereby covering the entire region. In the preferred method of repairing inquinal herniation, the mesh is attached bilaterally. Referring now to FIGS. 1 through 6, the dart type fasteners 11 of the fastening system of this invention are shown.

Figure 1:
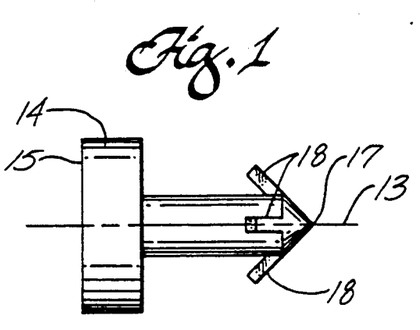
FIG. 1 is a front view of the dart fastener according to the present invention.
Figure 2:
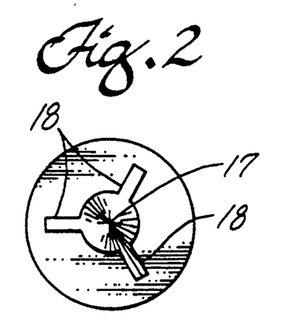
FIG. 2 is a top view of FIG. 1.

FIG. 1 is a side view illustration of dart fastener 11 and FIG. 2 is a top view. The dart fastener is preferably made of polypropylene. However, the dart may be made of stainless steel, or polydioxanone suture (PDS ®) which is a registered trademark of Johnson and Johnson. As can be seen in FIG. 1, dart fastener 11 has a shaft member 12 and a longitudinal axis 13. The shaft member 12 is integrally formed with the disc or head 14 at the second end 15 of the dart. At the first end 17 of the dart fastener, shaft member 12 has a plurality of anchor members 18 extending radially from the shaft at an approximate 45-degree angle with the longitudinal axis; anchor members 18 are spaced angularly about the longitudinal axis at equal angles.

Figure 3:
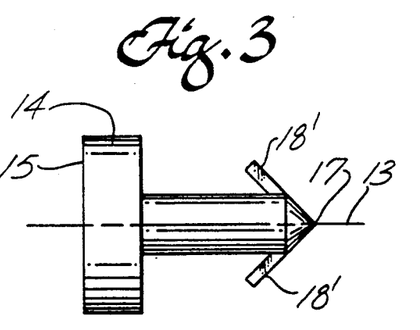
FIG. 3 is another embodiment of the dart fastener of the present invention.
Figure 4:
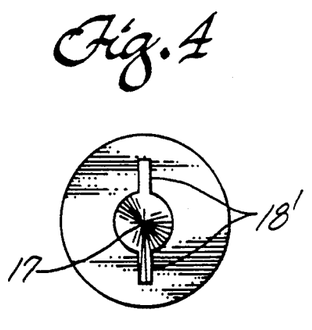
FIG. 4 is a top view of FIG. 3.
Figure 5:
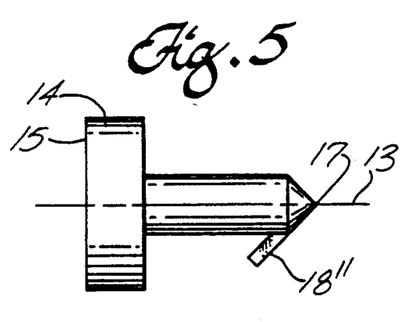
FIG. 5 is a front view of another embodiment of the dart fastener of the present invention.
Figure 6:
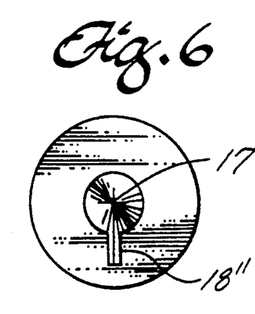
FIG. 6 is a top view of FIG. 5.

Other embodiments of dart fastener 11 are shown in FIGS. 3 through 6 and it can be seen in FIG. 3 that dart fastener 11 is comprised of two anchor members 18' which are spaced diametrically opposite from each other at the first end 17 of dart fastener 11 and extend radially from the longitudinal axis at an angle of approximately 45-degrees. In the embodiment as shown in FIGS. 5 and 6, the dart fastener has one anchor member 18" which extends in the same manner from shaft 12 as the embodiments previously described. Anchor members 18, 18', and 18" extend resiliently from the shaft 12 such that when the anchor member is compressed radially into shaft 12, the anchor member will be biased to spring back toward its equilibrium position. The anchor members are extended at an angle of approximately 45-degrees from the longitudinal axis of dart fastener 11 in the preferred embodiment. However, any angle would be appropriate less than 90° provided the dart could penetrate an interstice of the mesh prosthesis if used for laparoscopic hernia repair. Thus, when the dart fastener is inserted into body tissue, the anchor members will radially collapse such that the anchor member because of the resilience of the material will be biased to spring radially outward and the dart fastener will be captively held unidirectionally in the body fascia in much the same manner as a harpoon.

Since the dart fasteners are inserted laparoscopically into the preperitoneal space by insertion through trocars of diameters of 5 to 10 mm, the dimensions of the dart fasteners are of very small magnitudes. The diameter of shaft member 12 is preferably 1 mm with the anchor members having a length of approximately 1½ mm and the overall length of the dart fastener approximately 4 mm. The head or disc 14 of the dart fastener is preferably 3 mm in diameter and approximately 1 mm in thickness. The dart fasteners are made of a materials which are well-tolerated by the human body such as polypropylene, stainless steel, or "PDS" ® and which have the physical property of a sufficient modulus of resilience to store the elastic energy caused by the radial collapse of the anchor member.

Figure 9:
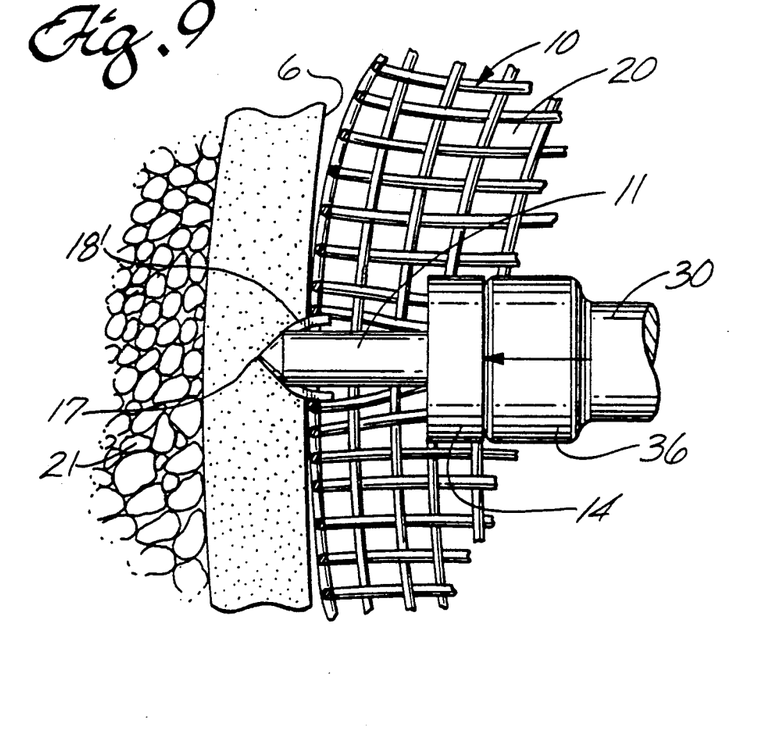
FIG. 9 is an illustration of the dart fastener being inserted through the mesh prosthesis and into body tissue.
Figure 10:
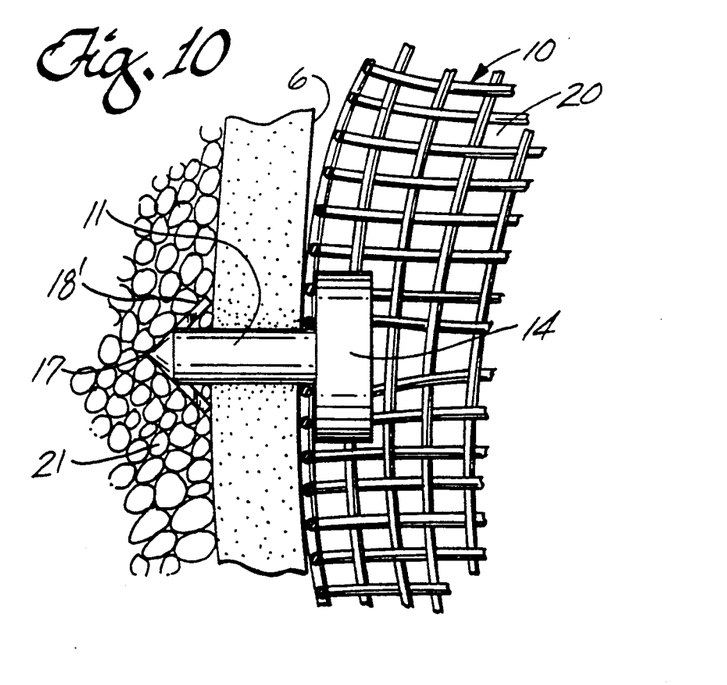
FIG. 10 is illustrates the dart fastener fixing the mesh prosthesis to body tissue.

The setting of dart fastener in body tissue is shown in FIGS. 9 and 10. In FIG. 9, it can be seen that mesh 10 contains numerous interstices 20 through which the first end 17 of dart member 11 passes before entering the posterior abdominal wall 6. As can be seen in FIG. 9, anchor member 18' collapses radially as the dart fastener passes through the mesh 20 and into the posterior abdominal wall. Referring to FIG. 10, which illustrates the dart fastener 11 after penetrating through the abdominal wall and into the body fascia 21, upon entering fascia 21 anchor members 18' are urged or biased to spring back to their equilibrium position thereby fixing the dart fastener to the body tissue and securing the mesh 10 to the posterior abdominal wall 6.

Figure 7:
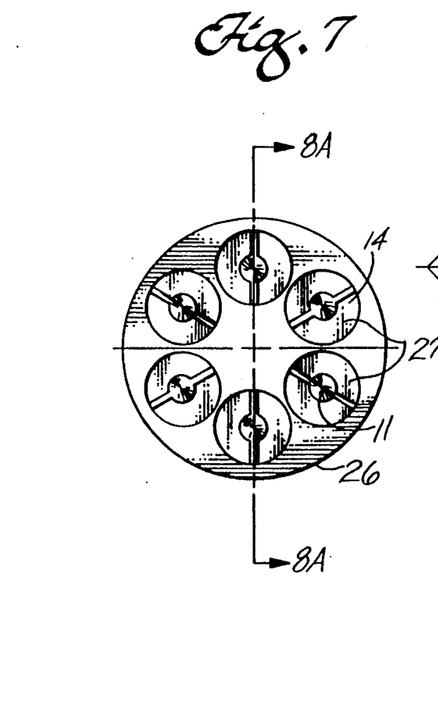
FIG. 7 is a front view of the setting tool of the present invention, illustrating the loaded cartridge at the distal end of the tool.
Figure 8:
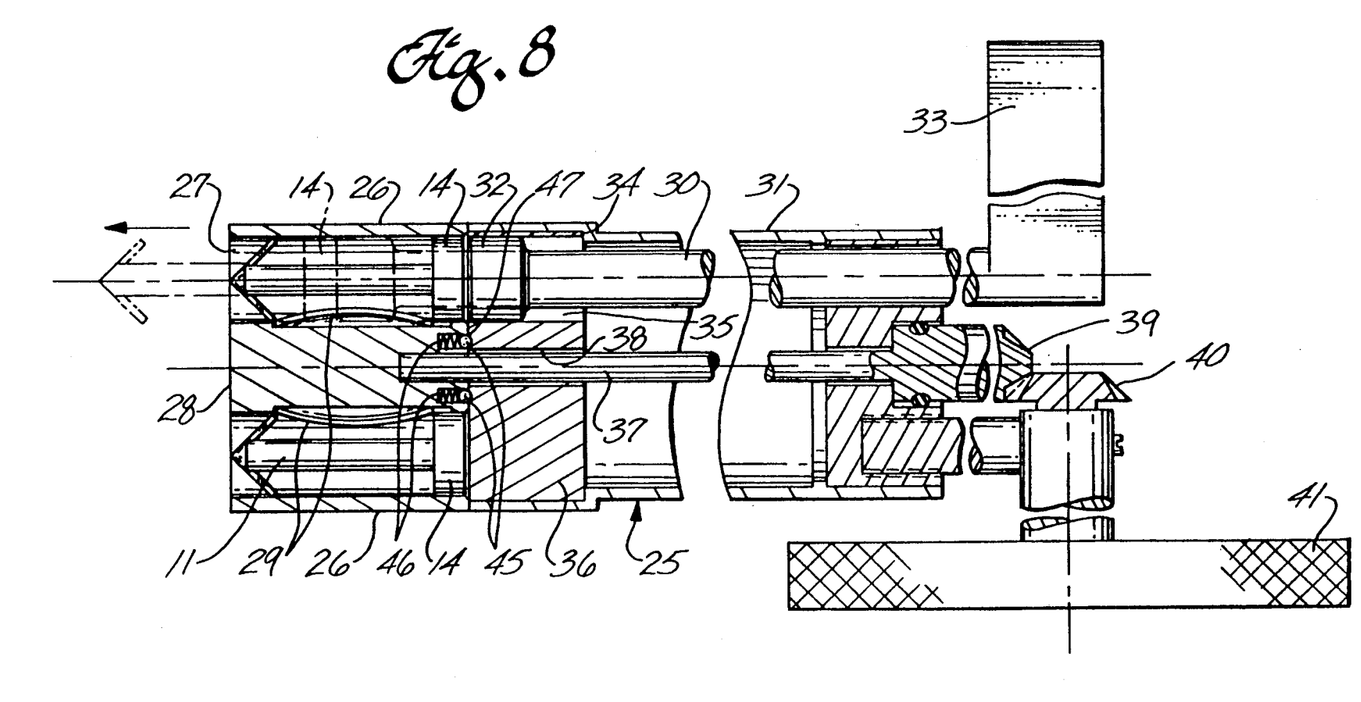
FIG. 8 is a cross-sectional view along line 8A—8A of FIG. 7 illustrating another embodiment of setting tool.

The delivery and fixation of dart fastener 11 laparoscopically is achieved by the use of a tool which can be inserted through a trocar and thereafter manipulated by the surgeon to seat the fastener. FIG. 8 illustrates the preferred embodiment of the dart fixation tool 25 of this invention. Dart fixation tool 25 is shown in partial cross-section taken along the line 8A—8A of FIG. 7. FIG. 7 depicts a front view of cartridge 26 which is loaded with dart fasteners 11 in a multiplicity of peripheral chambers 27 that extend longitudinally through cartridge 26 and are angularly spaced at equal intervals about the periphery of the cartridge 26. The diameter of chambers 27 is approximately equal to the diameter of the disc or head 14. To load cartridge 26, the dart fasteners 11 are inserted into the cartridge at the cartridge's distal end 28.

In the embodiment shown in FIG. 8, each chamber contains a leaf spring 29 to captively hold dart fastener 11; however, in another embodiment, dart fastener 11 may be captively held may by interference fit in chamber 27 through closely held tolerances between the head or disc 14 and the diameter of chamber 27. To remove a dart fastener from its captive chamber during the process of fixing the dart to body tissue, a plunger 30 is slideably mounted within housing 31. As shown in FIG. 8, if a force is applied to plunger 30, the head of the plunger 32 acts against disc 14 of dart 11 and forces the dart through the chamber by remaining in bearing contact with the head or disc 14 of dart fastener 11. In this manner, the dart is fixed to human tissue and plunger 30 is thereafter retracted through chamber 27 and into the housing 31.

Handle 33 is utilized by the surgeon in both applying the force to seat the dart fastener and for retracting plunger head 32 through the chamber 27 into housing 31. As can be seen in FIG. 8, a stop 34 is provided to prevent the plunger head 32 from further retraction into housing 31. The plunger head 32 after retraction into housing 31, is contained within longitudinal bore 35 of distal plug 36 which is carried by housing 31 by interference fit and in fixed relationship to the housing. The diameter of longitudinal bore 35 is approximately the same as the diameter of chamber 27; thus, when a chamber 27 is aligned with longitudinal bore 35, the plunger 30 may be directed into and through chamber 27 by the application of an external force at the handle 33.

Continuing with the description of dart fixation tool 25 illustrated in FIG. 8, a drive rod 37 is carried by housing 31 and extends through central bore 38 of distal plug 36. Drive rod 37 is threaded into a cartridge 26 such that rotation of drive rod 37 will rotate cartridge 26 with respect to housing 31. As can be seen in FIG. 8, drive rod 37 is driven at its proximate end by a gear train comprised of bevel gear 39 which is engaged by gear 40 where gear 40 in turn is carried by housing 31 and connected to knurled knob 41 for rotation therewith. Thus, the surgeon, by rotating knurled knob 41 positions cartridge 26 relative to the housing 31 to align a chamber 27 with the longitudinal bore 35 of distal plug 36. To mechanically achieve this alignment, the cartridge 26 carries a pair of balls 45 which are biased into engagement with distal plug 36 by springs 46. Distal plug 36 contains a series of detents 47 which are located radially about the central axis of distal plug 36 and spaced equally such that chamber 27 alignment with longitudinal bore 35 occurs when balls 45 are biased into the detents 47. This permits the surgeon to index carriage 26 after seating a dart fastener by rotation of knurled knob 41, and thus align the next loaded chamber for receiving the plunger head 32.

Figure 8A:
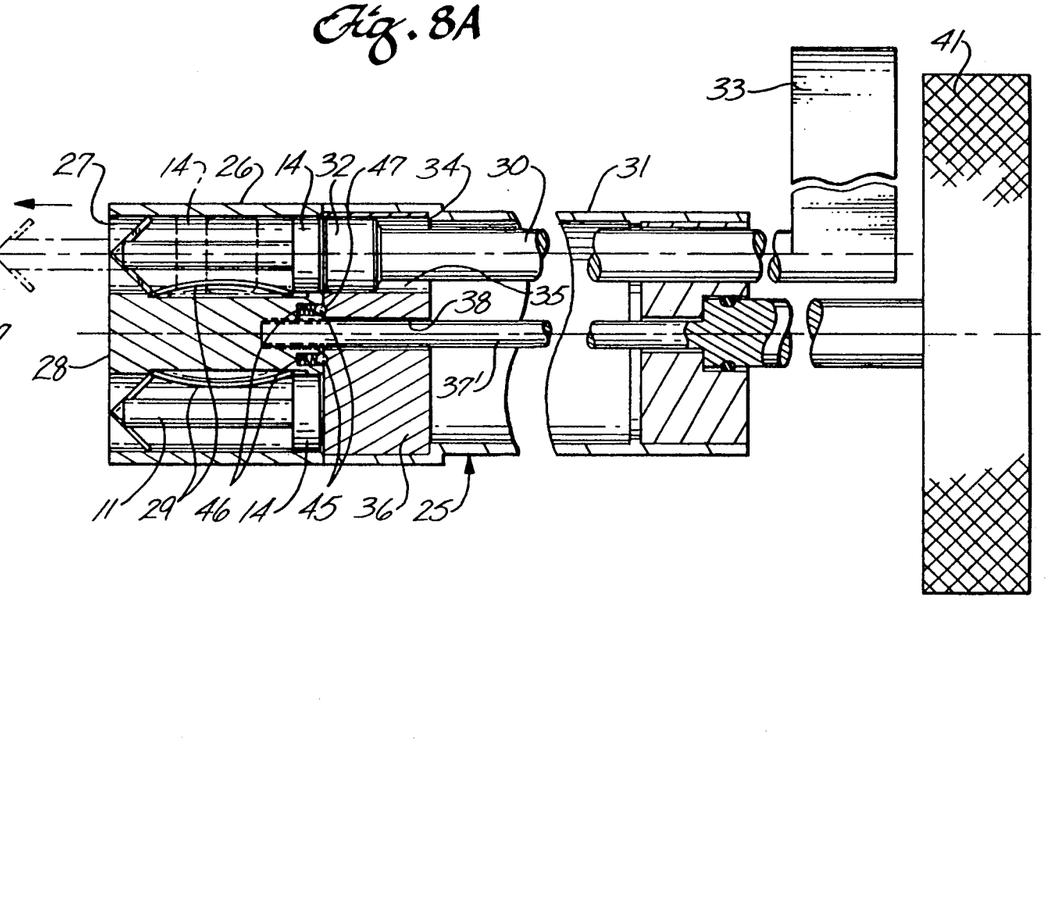
FIG. 8A is a cross-sectional view along the line 8A—8A of FIG. 7 illustrating one embodiment of the setting tool of the present invention.

Another embodiment of the dart fixation tool of this invention is illustrated in FIG. 8-A. In this embodiment, driver rod 37' is attached directly to knurled knob 41, to permit direct rotation of the cartridge 26 without the utilization of a gear train.

Figure 11:
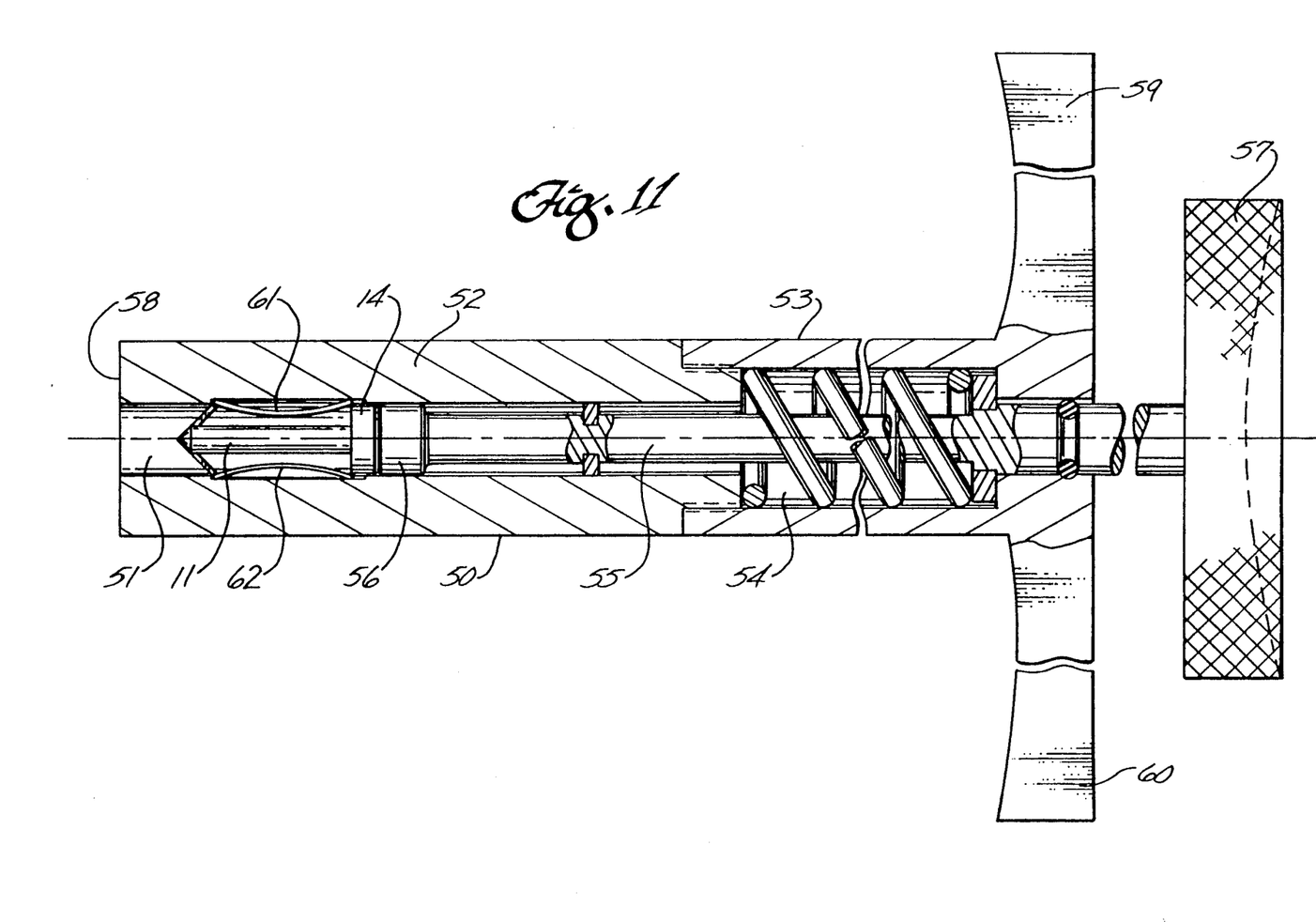
FIG. 11 is a cross-sectional view of another embodiment of my present invention for setting a dart-like fastener.

FIG. 11 is still another embodiment of a fixation tool for use in the fastener system of this invention. In this embodiment of the invention, dart fixation tool 50 carries a single dart fastener 11 in longitudinal bore 51. Bore 51 extends through cylinder 52 which threads into grip head 53. Grip head 53 has an internal chamber 54 which communicates with longitudinal bore 51 thereby providing a continuous cavity or passage through both grip head 53 and cylinder 52. To provide for ejection of a fastener from the cavity, a plunger 55 with plunger head 56 is slideably carried by the assembly of cylinder 52 and the grip head 53. At its proximate end, plunger 55 is attached to thrust knob 57 to which an external force may be applied to move plunger 55 through longitudinal bore 51 to eject dart fastener 11 from the tool at its distal end 58. A helical spring 63 is held within chamber 54 in compression by bearing surface 64 located at the proximate end of cylinder 52 and by washer 65 which is mounted on plunger 55 to restore the plunger head to its initial position before application of the external force. A pair of radially extending shoulder members 58 and 59 project from grip head 53 to provide a counter reactive grip for the surgeon during the course of applying a force to thrust knob 57.

In operation the surgeon applies a continuous force by thumb pressure to thrust knob 57 which causes plunger head 56 to bear against disc 14 of dart fastener 11. The continuous application of external force overcomes the spring force exerted by leaf springs 61 and 62 and drives dart fastener 11 through longitudinal bore 51 and into body tissue.

Figure 14:
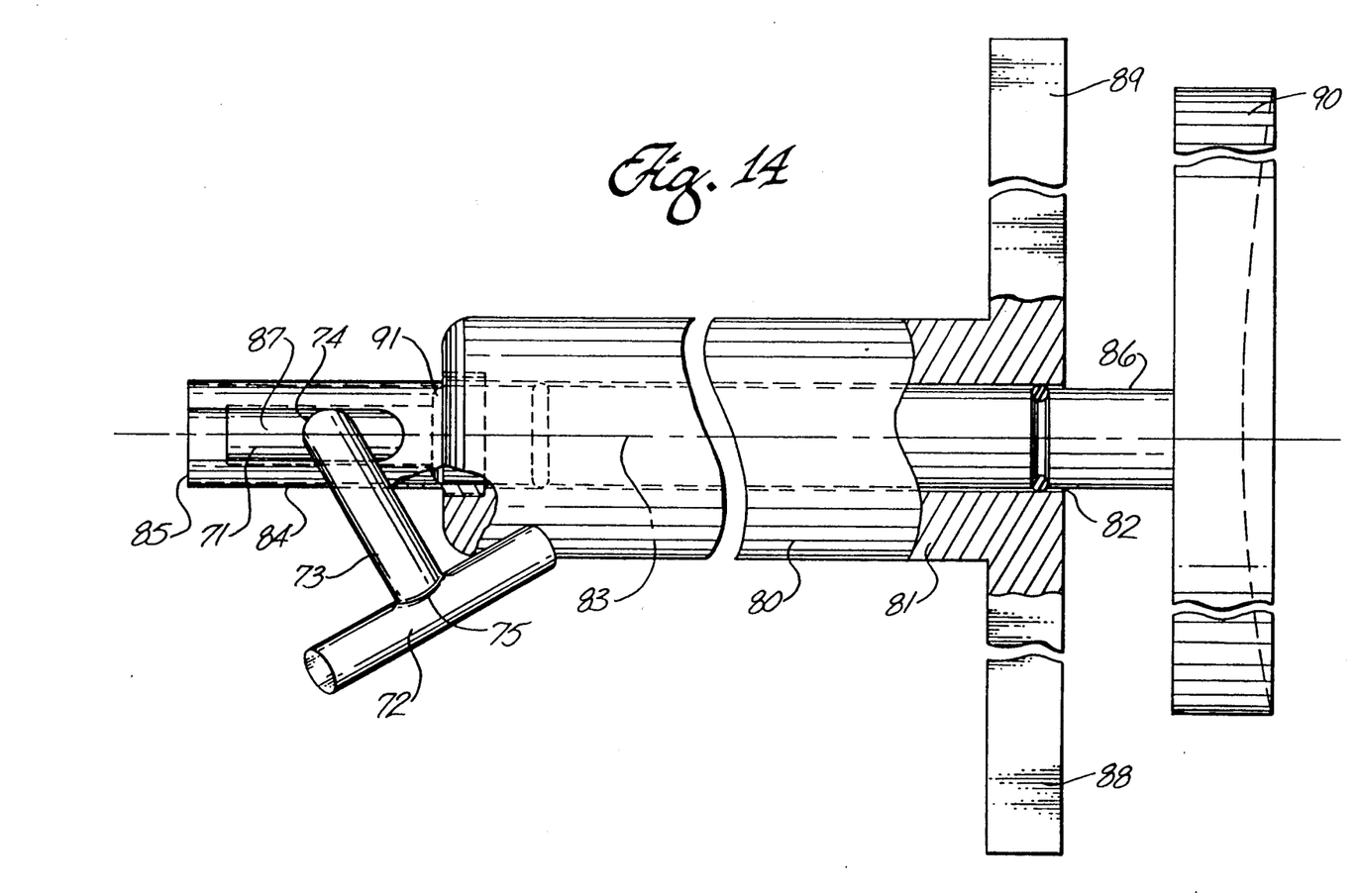
FIG. 14 is a partial cross-sectional view of my invention of a fixation tool for inserting an H-shaped fixation fastener through body tissue.
Figure 15:
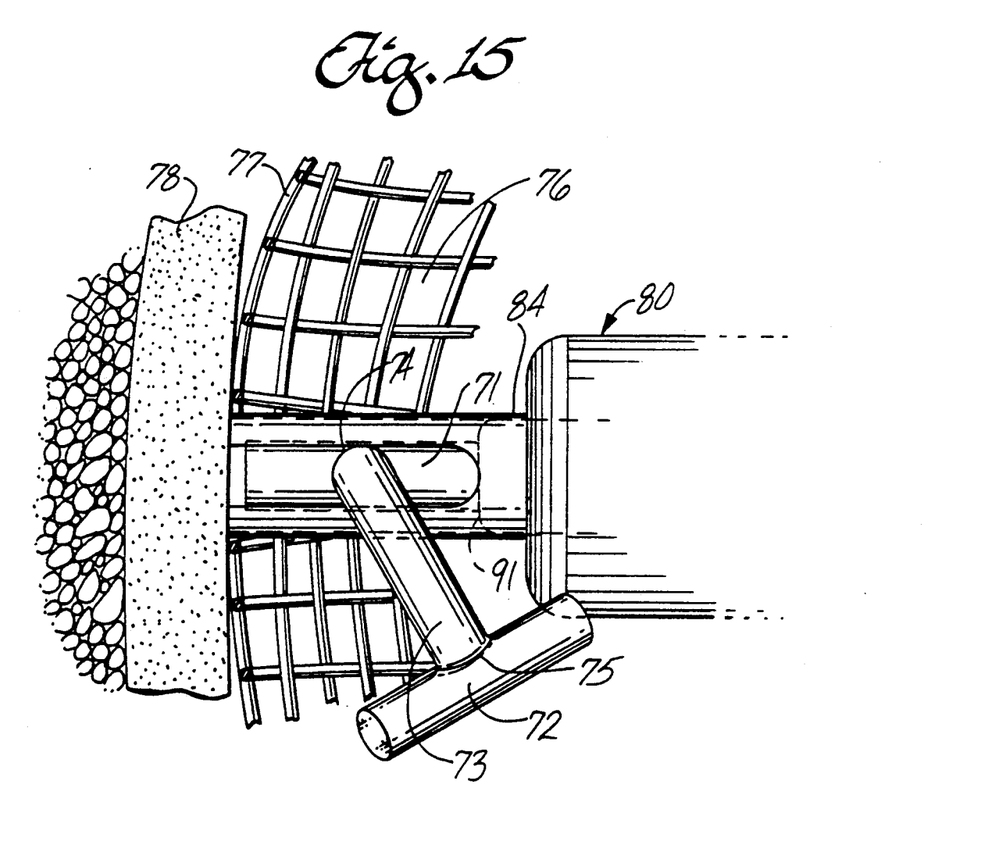
FIG. 15 illustrates the H-shaped fastener of my invention positioned for insertion through an interstice of a mesh prosthesis and into body tissue.
Figure 16:
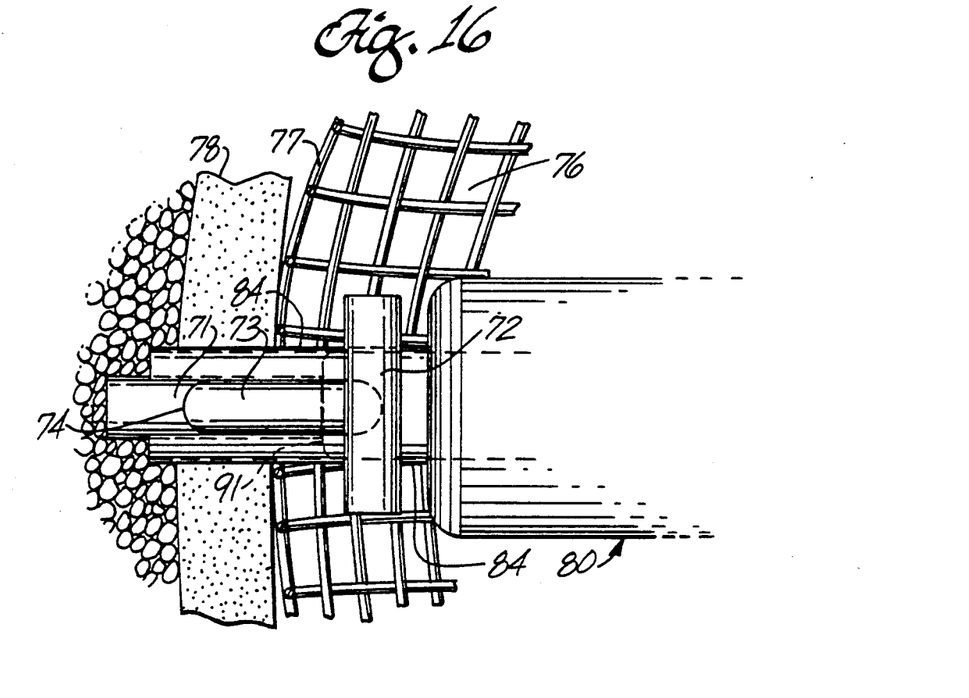
FIG. 16 illustrates the H-shaped fastener of my invention after insertion into body tissue and before entering the fascia.
Figure 17:
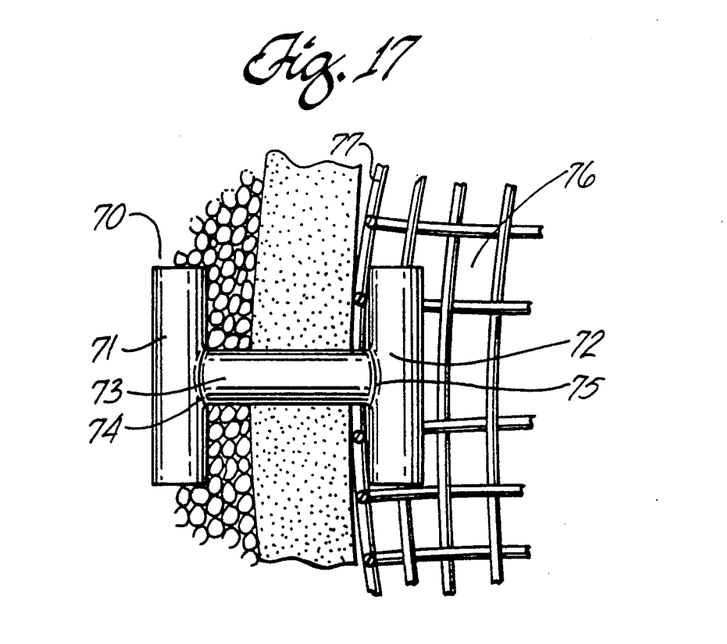
FIG. 17 illustrates the H-type fixation fastener of my invention after being seated in body tissue.

Another embodiment of the fastener system of this invention is shown in FIGS. 15, 16 and 17. As can be seen in FIG. 17, a fixation fastener 70, made of a material such as polypropylene, stainless steel or polydioxanone suture having the physical property of a sufficient modulus of resilience to store the elastic energy caused by bending or torsion and having the shape of an H, is composed in part by a pair of essentially parallel cylindrically shaped shaft members 71 and 72 which are preferably 1 mm in diameter and 4 mm in length. A bridge shaft 73 having a diameter of 1 mm interconnects shafts 71 and 72 and forms an integral joint with each of shafts 71 and 72 at its intersections. The joints 74 and 75 because of the resiliency of the material permit shafts 71 and 72 to pivot about the joints but are biased by the resiliency of the material such that the shaft members and the bridge member will be biased to return to an H-shape. Thus, fixation fastener 70 has an equilibrium position in the H-shape shown in FIG. 17 and the shaft members are resiliently joined together such that the internal elastic forces of the material will tend to bias the shaft members back to the equilibrium position in the event they are disturbed therefrom. To set fixation fastener 70 in body tissue, either of the shaft members 71 or 72 may be driven by an external force through an interstice 76 of the mesh prosthesis 77. The external force may be applied to either shaft 71 or 72 by setting tool 80 which is more definitively illustrated in FIG. 14.

Referring to FIG. 14, it can be seen that setting tool 80 has a housing 81 with a longitudinal cylindrical cavity 82 extending axially through the housing along longitudinal axis 83. A needle member 84, having an internal axially extending bore 85 communicates with cavity 82 of the housing forming a continuous cylindrical axially extending passage through setting tool 80 through which plunger 86 may be extended or retracted by a member of the surgical team.

At the distal end of setting tool 80 an axially extending slot 87 is provided which permits the setting tool to be loaded with fixation fastener 70 by extending either shaft 71 or 72 of the fixation fastener into the opening at the distal end 85 of needle tip 84. The bridge shaft 73 of the fastener extends through the slot 87 which has a slot thickness substantially the same as the diameter of bridge shaft 73 such that the fastener 70 is captively held in the slot by an interference type fit. To drive fastener 70 into human tissue, the distal end of setting tool 80 is inserted into a trocar of sufficient diameter to accommodate the diameter of the tool. By the surgeon gripping shoulder members 88 and 89 which extend radially from the proximate end of housing 81, and pressing thumb disc 90, slideably mounted plunger 86 within the housing 81 is forced to move axially toward the distal end 85 of the tool. Thus, plunger head 91 is brought into bearing contact with shaft 71 of fixation fastener 70 as more clearly shown in FIG. 15.

Although not shown in the Figures, housing 81 of setting tool 80 may also be structured, for retraction in a manner similar to the tool as illustrated in FIG. 11. Thus, by utilizing a cylinder member and grip head as shown in FIG. 11, housing 81 could be adapted to incorporate a helical spring and washer for applying a restoring force to plunger 86 after thumb disc 90 is released.

Referring now to FIG. 16, it can be seen that needle member 84 in the setting process of fastener 70 is inserted through an interstice 76 of the mesh prosthesis 77 by the surgeon. By applying continuous pressure to thumb disc 90, the surgeon forces shaft 71 of the fastener into body tissue 78; shaft 71 will thereafter under continued pressure go through body tissue 78 until the shaft 71 is in the fascia and bridge member 73 has extended through body tissue 78 as shown in FIG. 17. The surgeon then withdraws plunger 86 into the housing 81 and retracts setting tool 80 through the trocar for reloading.

Thus, referring again to FIG. 13, and continuing with the method to attach the mesh prosthesis to the posterior abdominal wall, the mesh as previously described was introduced into the cavity between the peritoneum and the posterior wall through a 10 mm trocar located in the midline in the suprapubic position. A 10 mm laparoscope with a 30-degree angle lens was then inserted through the 10 mm trocar and two grasper tools used to grasp the mesh were inserted into the cavity through two 5 mm trocars or sheaths which were placed in the left midclavicular and right midclavicular lines respectively in the pelvis. The mesh prosthesis is fixed to the abdominal wall by inserting dart fastener 11 approximately 2 cm lateral to femoral ring 2; this is accomplished by inserting fixation tool 25 through either the right or left 5 mm trocar and holding the mesh with the grasper tool inserted through the other 5 mm trocar. After the dart fastener 11 has been placed laterally of the femoral ring by the surgeon, the mesh which is of pre-selected dimensions may be manipulated to cover the entire pelvis bilaterally from, for example, the right side of the inguinal cord across the midline to the left side of the cord. Fixation tool 25 is then inserted through the appropriate 5 mm trocar to set a dart fastener to fix the mesh to Cooper's ligament on both the left and right sides and thereafter to the abdominal wall 6 on both the left and right sides of the inguinal region.

While I have shown alternative embodiments of the present invention, it is to be understood that they are subject to many modifications without departing from the scope and spirit of the claims as recited herein.

What is claimed is:

1. A fastener system for attaching a mesh prosthesis or tissue to body tissue comprising in combination:
   a) a fastener comprising an H-shaped member made of a material having the property of a sufficient modulus of resilience to absorb the elastic energy produced by a deformation of said H-shape to restore said member to said H-shape, said H-shaped member comprising a pair of oppositely spaced shaft members, a bridge shaft interconnecting said shaft members forming a resiliently flexible joint with each said shaft member, and where said shaft members are so dimensioned and proportioned that each of said shaft members has sufficient columnar resistence to bending to permit insertion of said shaft member into said body tissue; and
   b) a setting tool comprising, a housing having a longitudinal axis and a proximate and distal end, a needle member having a central axis carried by said housing adjacent said distal end of said housing so as to form the distal tip of said setting tool, said needle member having a conduit extending axially therethrough and an axial open slot extending through the periphery of said needle member, said slot communicating with said conduit where said slot is axially bounded in a direction proximate of said distal tip and so proportioned and dimensioned to captively hold said fastener, and setting means slideably carried by said housing and responsive to external force for applying a thrust force axially within said needle member to said fastener so as to eject said fastener from said slot and into said body tissue.

2. The combination recited in claim 1 wherein said material is polypropylene, stainless steel, or polydixoanone suture.

3. The combination recited in claim 1 wherein said setting means further comprises a plunger member adapted for axial extension through said conduit, a washer mounted to said plunger member, and a helical spring compressively bearing against said washer member and said housing for applying a restoring force to said plunger.

4. The combination recited in claim 3 wherein said housing has an axially extending cavity therethrough where said cavity communicates with said conduit forming an axially extending passageway.

* * * * *